US006551819B1

(12) United States Patent
Simmet

(10) Patent No.: US 6,551,819 B1
(45) Date of Patent: Apr. 22, 2003

(54) CONTAINER FOR SEMEN AND OTHER BIOLOGICAL LIQUIDS

(75) Inventor: Ludwig Simmet, Verona, WI (US)

(73) Assignee: Minitube of America, Inc., Verona, WI (US)

( * ) Notice: Subject to any disclaimer, the term of this patent is extended or adjusted under 35 U.S.C. 154(b) by 20 days.

(21) Appl. No.: 09/606,831

(22) Filed: Jun. 29, 2000

(51) Int. Cl.[7] .................................................. C12M 1/24

(52) U.S. Cl. .................... 435/307.1; 222/143; 222/527; 222/572; 222/541.9; 383/32; 383/36

(58) Field of Search ........................... 435/288.1, 304.1, 435/307.1, 309.1; 422/102; 222/527, 566, 572, 107, 143, 541.6, 541.9; 604/762, 906; 383/36, 32; 215/10, 47, 48; 206/505, 520, 820

(56) References Cited

U.S. PATENT DOCUMENTS

| | | | | | |
|---|---|---|---|---|---|
| 2,349,962 | A | * | 5/1944 | Harris | 222/107 |
| 2,566,632 | A | | 9/1951 | Propp | |
| 3,584,211 | A | * | 6/1971 | Rauhut | 222/541.6 |
| 3,884,231 | A | | 5/1975 | Peters | |
| 3,917,120 | A | * | 11/1975 | Larenz et al. | 206/484 |
| 4,061,144 | A | * | 12/1977 | Strickman et al. | 604/262 |
| 4,428,507 | A | | 1/1984 | Sneider | |
| 4,641,362 | A | | 2/1987 | Muller | |
| 4,798,605 | A | | 1/1989 | Steiner | |
| 4,894,061 | A | | 1/1990 | Dobruskin | 604/403 |
| 5,006,117 | A | | 4/1991 | Cassou | 604/403 |
| 5,029,738 | A | * | 7/1991 | Dillon | 222/215 |
| 5,577,636 | A | * | 11/1996 | Fukuoka et al. | 222/107 |
| 6,076,712 | A | * | 6/2000 | Esber et al. | 222/527 |

FOREIGN PATENT DOCUMENTS

| | | |
|---|---|---|
| DE | 19527943 | 2/1997 |

OTHER PUBLICATIONS

Spermnotes, Equine Edition newsletter, Spring 1999.
Penetrating Innovations, Minitube 2000, Minitube of America (2000).
Artificial Insemination brochure, Minitüb., May, 1997.
Artificial Insemination brochure, Minitüb, 1999.
Artificial Insemination of Horses brochure, Minitüb (No date provided).
Embryo Transfer brochure, Minitüb, 1999.
International Preliminary Examination Report for PCT/US01/20337 (Oct. 14, 2002).

* cited by examiner

*Primary Examiner*—William H. Beisner
(74) *Attorney, Agent, or Firm*—Lathrop & Clark LLP

(57) ABSTRACT

A container for biological fluids useful in artificial insemination is disclosed. The inventive container has a nozzle for delivery of the biological liquid, wherein the nozzle has means for bending such that the container may be used in a vertical position while attached to a horizontal catheter. The nozzle also has means to facilitate opening the tube without tools.

5 Claims, 2 Drawing Sheets

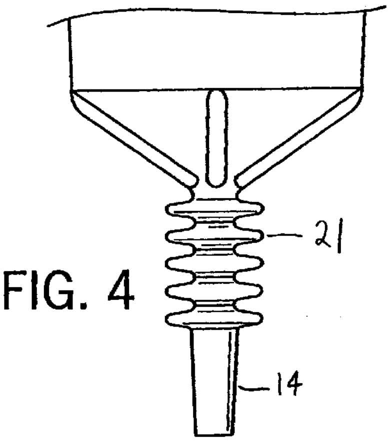
FIG. 4
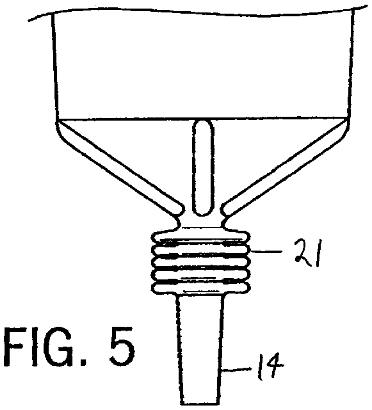
FIG. 5
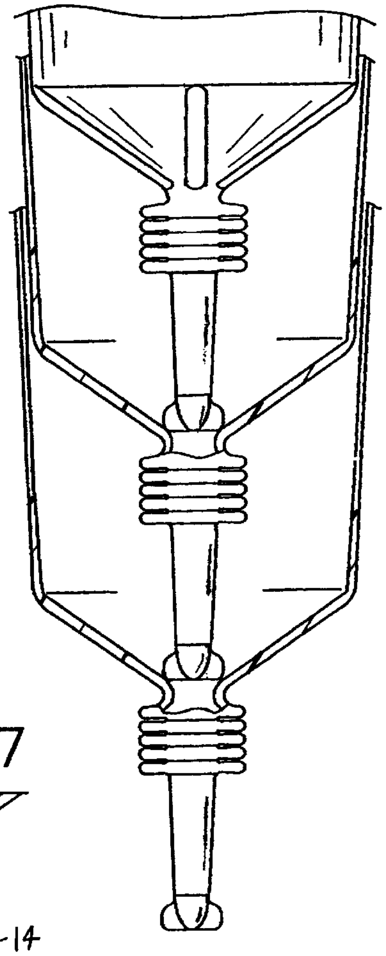
FIG. 6
FIG. 7
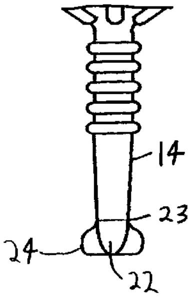
FIG. 8
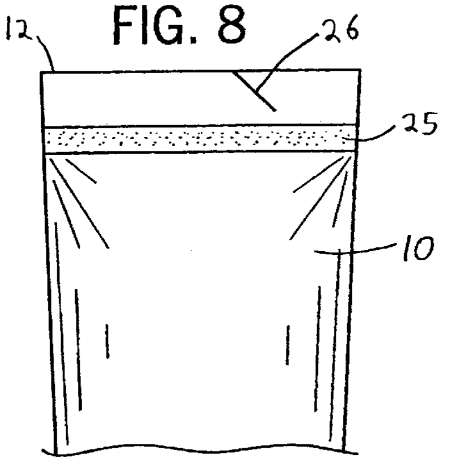

CONTAINER FOR SEMEN AND OTHER BIOLOGICAL LIQUIDS

FIELD OF THE INVENTION

The present invention relates to a container for biological liquids, more particularly, biological liquids used in the artificial insemination of animals.

BACKGROUND OF THE INVENTION

Artificial insemination and embryo transfer involves the delivery of biological cells useful for the purposes of procreation (such as semen or embryos) to the reproductive tract of a female animal. Typically, especially in the case of inseminating livestock, these biological cells are stored in sealed containers prior to use. Several suitable containers are known.

In particular, U.S. Pat. No. 5,006,117, issued to Cassou, discloses a container for biological liquids comprising a hollow body of elastomeric material including a tubular intermediate part, rounded ends, and a portion adapted to be perforated by a cannula. The improvement of the device of U.S. Pat. No. 5,006,117 comprises the interior and exterior surfaces of the container being smooth and curved throughout and the means performable by a cannula comprising a thick wall portion. In practice, this container is a flexible flat plastic bag which is adapted to seal around a specially designed catheter.

Another container, available from Minitube, comprises a plastic semen tube having a hollow body with at least partially collapsible walls, a first end adapted for filling and adapted for sealing and a second end having an integrally molded rigid nozzle, and in which the second end is reinforced to be more rigid than the hollow body walls. The Minitube container is heat sealed, across the end opposite the rigid nozzle, after being charged with the biological liquid.

During the insemination procedure of, for example, swine, the container is opened and attached to a semi-rigid tube or catheter which has been inserted into the animal being bred. Typically the container is inserted in-line with the catheter which is positioned to accommodate the animal's anatomy. At best, the catheter is positioned horizontally, but with swine, the distal end of the catheter generally is positioned approximately 30° below horizontal. Muscular contractions aid in drawing the biological liquid into the sow's body. Desirably, the container would be positioned vertically to facilitate gravity flow, thereby assisting the transfer of the biological fluid from the container to the sow.

However, while a number of methods of achieving a vertical position for the container have been used, none of these methods are totally acceptable. For example, flexing the semi-rigid catheter is believed to cause pain and possible damage by applying strain to the soft tissues of the animal's body. On the other hand, flexing or bending the container tends to cause the container to kink thereby restricting the flow of the biological liquid from the container. Still another method is to connect a long section of flexible tubing between the container and the catheter. This method has the disadvantages of: (i) increasing the materials that have to be cleaned or disposed of between insemination procedures; (ii) increasing the loss of biological cells due to residue on the walls of the tubing; and, (iii) increasing the time required to complete the insemination procedure.

One hallmark of the current invention is a container that can be positioned vertically in respect to the insemination catheter without causing pain to the animal or hindering the delivery of the biological fluid to the animal being bred.

SUMMARY OF THE INVENTION

A container for biological liquid is disclosed. The container comprises a hollow body of plastic material, wherein the hollow body comprises at least a first and a second end, the first end being adapted for receiving the biological liquid and further adapted for sealing, and a rigid closed nozzle that is integrally molded to the second end of the hollow body, wherein the nozzle has means for bending the nozzle without forming any kinks in either the nozzle or the hollow body and wherein the nozzle is adapted for opening. Optional, but desirable, features of the container include means for easy manual opening of the container and flexible container walls.

The container of this invention advantageously may be used to store and transport semen for the artificial insemination of animals.

BRIEF DESCRIPTION OF THE DRAWINGS

FIGS. 4 and 5 show an embodiment of the inventive container wherein the nozzle comprises accordion folds. FIG. 4 shows the accordion folds in an expanded position and FIG. 5 shows the accordion folds in a collapsed position.

FIG. 6 is a partially cut away front perspective view of a nesting arrangement of the inventive container shown in FIG. 5.

FIG. 7 shows a detailed front perspective view of an inventive container nozzle which has been adapted for ease of manual opening.

FIG. 8 is a partial expanded view along the line 8 of FIG. 1.

DETAILED DESCRIPTION OF THE INVENTION

As used herein, the term "kink" refers to a sharp bend in a hollow object having an open cross section. A kink is characterized by a straight crease along a chord or diameter of the original cross section of the hollow object such that the open area of the hollow object is significantly decreased or eliminated.

The term "biological liquid" refers to biological fluids or biological cells in a fluid medium. Examples of such biological liquids include blood, plasma, and cultured tissues. Preferably, the biological liquid is a cultured tissue such as biological cells useful for the purposes of procreation such as semen, oocytes, embryos or combinations thereof. These biological cells useful for the purposes of procreation may be present alone or in combination with any culture media, antimicrobial agents fillers, extenders, solvents, dispersants or diluents.

The inventive container has at least a hollow body, a first end adapted for filling and also adapted for sealing and a second end having an integrally molded rigid nozzle. The containers are conveniently provided to stud farms with the nozzle (second) end sealed and the opposite (first) end open. The biological liquid may then be filled into the tube by any convenient means, such as manually pouring the liquid or depositing the liquid with an automatic filler. The filled tube is then sealed along the second end by any appropriate sealing means, preferably by heat sealing ultrasound, infrared or wire sealers.

The walls of the container body are typically made from a non-spermicidal material, preferably a plastic. Examples of suitable plastics include polyolefins (such as polyethylene, polypropylene etc.), polyvinylchloride, nylons, polyfluorocarbons, thermoplastic polyurethanes, polystyrene, elastomers, cellulosic resins, acrylic resins and silicones, preferably polyolefins and elastomers.

Preferably, the walls are thin enough to at least mostly collapse under the influence of a partial vacuum in the container body. During an artificial insemination procedure, the drainage of the biological fluid, and the pumping action of muscular contractions within the animal, are believed to exert a partial vacuum within the container. If the walls are too rigid, this partial. vacuum persists and hinders the flow of the biological liquid from the container. The collapse of flexible walls relieves the partial vacuum and thereby facilitates the rapid flow and near complete drainage of the biological fluid from the container.

The rigidity of the walls is conveniently controlled by the wall thickness. The desired wall thickness depends on the application but one skilled in the art can readily determine a wall thickness that permits the container wall to collapse during insemination. An example of a tube having a suitable wall thickness to allow the desired wall collapse is the ULTRAFLEX™ boar semen tube available from Minitube.

Figure 3:
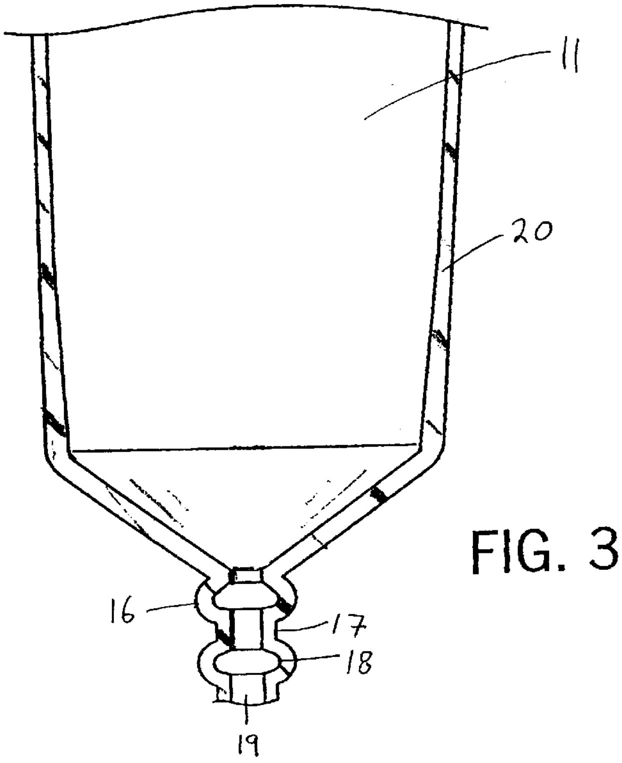
FIG. 3 shows a partial cross section along the lines 3 shown in FIG. 1.

In a preferred embodiment, the body wall thickness is increased in the vicinities of both ends of the tube. The increased body wall thickness near the second end of the tube provides reinforcement to facilitate inserting the tube nozzle into an artificial insemination catheter. Preferably, the body wall thickness is greater near the second end then near the first end. The increased body wall thickness near the first end facilitates filling of the tube by providing a more stable opening and also facilitates sealing the tube. Preferably, the wall thickness in this embodiment tapers (as shown in FIG. 3) from the thickness required to obtain partial collapse of the wall under a partial vacuum to the thickness required to facilitate the insertion of the container nozzle. An example of a tube having suitable wall thickness at both ends of the tube is the ULTRAFLEX™ boar semen tube available from Minitube.

The container of this invention comprises a rigid nozzle that may be bent without forming kinks in either the nozzle or the tube. Any means for bending the nozzle is usable in this invention provided that the bend in the nozzle does not form kinks in either the nozzle or the container. Preferably the means for bending the nozzle is either at least one corrugation or at least one accordion fold.

Figure 2:
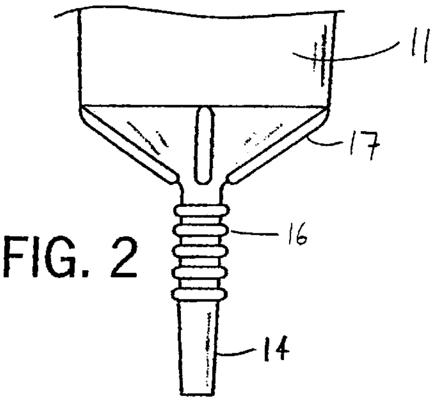
FIG. 2 shows a side perspective view of the nozzle and of an inventive container wherein the nozzle is in a straight orientation with the semen tube.

The term "corrugation" refers to a rounded protrusion extending either inward or outward, preferably outward, from the nozzle surface. Typical corrugations are shown in FIGS. 2 and 3. The wall thickness in the corrugation is generally substantially equal to, or thinner than, the wall thickness in the straight sections of the nozzle.

Accordion folds are substantially V-shaped folds as shown in FIGS. 4 and 5.

The nozzle must also have sufficient rigidity to allow insertion of the nozzle into an insemination catheter. Preferably, the container is reinforced to assist an insertion of the nozzle into the insemination catheter. Such reinforcement may conveniently be provided by increasing the body wall thickness (as shown in FIG. 3) and/or by reinforcement ribs on the second end (as shown in FIG. 2).

In a preferred embodiment, the nozzle tip has means to facilitate opening the nozzle. Such opening means are typically weak areas in the nozzle wall and/or leverage arms (e.g., tabs or flanges) on the nozzle. Preferably, such opening means facilitate easy manual opening of the nozzle without recourse to tools. In a most preferred embodiment, the nozzle is scored and provided with flanges, as shown in FIG. 7, to assist in manual opening of the inventive container. The score line is preferably located such that the means for bending is located between the score line and the hollow body. This embodiment allows the user to avoid cutting the container nozzle with a knife thereby decreasing the opportunity for bacterialogical or semen cross contamination of the semen sample stored in the tubes.

A boar semen tube, which is a preferred embodiment of the inventive container, is described in more detail in the Figures. This preferred embodiment is an improvement on the Minitube plastic semen tube having a hollow body with at least partially collapsible walls, a first end adapted for filling and adapted for sealing and a second end having an integrally molded nozzle, and in which the second end is reinforced to be more rigid than the hollow body walls.

Figure 1:
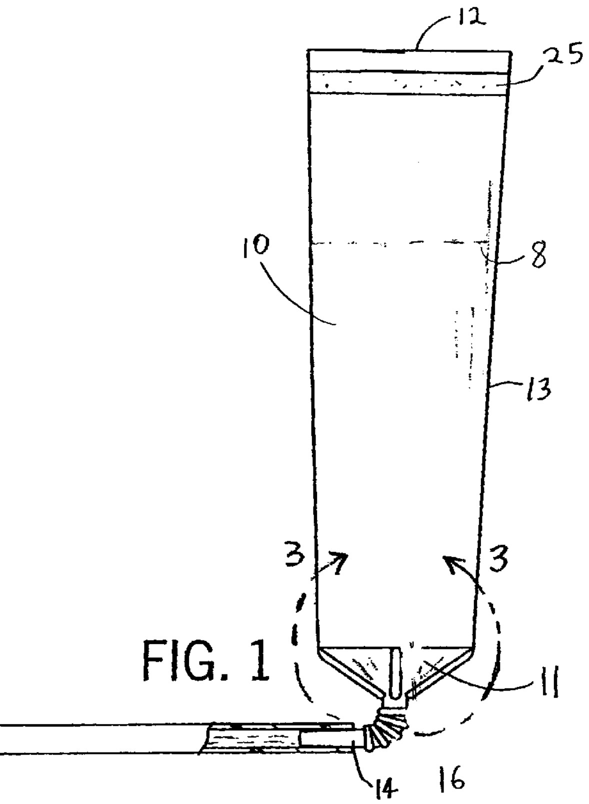
FIG. 1 shows a partially cut away front perspective view of a horizontal insemination catheter wherein an inventive container has been inserted and the container has been rotated to a vertical position.

As shown in FIG. 1, the semen tube 10 comprises a second end 11 wherein the nozzle is located, a first end 12 and a body 13. During an artificial insemination procedure, the nozzle 14 is inserted into a horizontal insemination catheter 15 which has been inserted into the animal's body. Conveniently, insertion of the nozzle into the catheter is accomplished with the semen tube in a horizontal position and the nozzle in a straight alignment along the longitudinal axis of the semen tube. The semen tube may then be rotated into a vertical position as shown in FIG. 1. Bending means 16 (here shown as corrugations) permits the semen tube to be rotated to a vertical position without forming kinks in the nozzle 14 or the semen tube body 13.

FIG. 2 shows a detailed view of second end 11. Nozzle 14 comprises multiple corrugations 17 as the bending means. Ribs 18 are provided to provide greater rigidity to end 11 and thereby assist in inserting nozzle 14 into an insemination catheter.

FIG. 3 shows a cross section of the embodiment of FIG. 1. The corrugations 16 protrude out from the straight sections of nozzle 17. Preferably, as shown, the inner surfaces 18 of corrugation 16 also protrude outward such that the wall thickness in the corrugated area 16 is similar to the wall thickness in straight areas 17. This structure of the corrugation 16 permits bending of the nozzle without kinking or constricting the flow channel 19 of the nozzle. FIG. 3 also shows a preferred embodiment wherein the tube wall 20 is formed to be thicker near the second (nozzle) end 11. This increased thickness at the nozzle end provides greater strength and rigidity and assists in inserting the nozzle into an insemination catheter.

Another embodiment of the container of this invention is shown in FIGS. 4 and 5. Here, the bending means on nozzle 14 consists of a series of accordion folds. These folds are shown in an expanded position in FIG. 4 and in a collapsed position in FIG. 5. The collapsed position shown in FIG. 5 is advantageous in decreasing the storage space required for the tubes prior to filling. In particular, as shown in FIG. 6, the collapsed position facilitates stacking the open tubes in a nested position.

FIG. 7 shows a preferred embodiment wherein the nozzle is adapted for ease of manual opening. Nozzle 14 ends in tip 22. A score line 23 demarks tip 22 from nozzle 14 and provides a weak point for the nozzle to break under manual force. Tabs 24 may be provided on tip 22 to facilitate the manual application of a torque or other sideways force. Tabs 24 also prevent the stacked tubes, as shown in FIG. 6, from nesting too tightly.

FIG. 8, which shows first end 12 above line 8 of FIG. 1. After filling, first end 12 of the tube is sealed 25 preferably by heat sealing. In a preferred embodiment, a cut 26 is provided through both walls on first end 12 to facilitate tearing open the heat seal during the insemination procedure thereby releasing the vacuum that which will form inside of the semen tube. Preferably, the cut is at an angle less than 90° (i.e., less than perpendicular) to the seal, more preferably about 45°.

The invention claimed is:

1. A stack of biological liquid containers, comprising:

a first container having a hollow body of plastic material having a sealable first end through which biological liquid is introduced and a second end having an integrally molded nozzle having an inner diameter, wherein a wall connects the first end and the second end, portions of the nozzle which define a section which bends without forming kinks, the nozzle terminating in a tip having at least one tab extending therefrom, the tab being severable from the tip, the tip with the tab having a dimension which is greater than said nozzle inner diameter; and a second container, substantially identical to the first container, and received within the first container, wherein the second container tip tab engages against the first container second end, the second container tip with tab thus being too large to be inserted into the inner diameter of the first container nozzle.

2. The stack of containers of claim 1, wherein in each container, the section which bends without forming kinks comprises either at least one accordion fold, at least one corrugation, or a combination thereof.

3. The stack of containers of claim 1, wherein in each container, the section which bends without forming kinks comprises a plurality of accordion folds.

4. The stack of containers of claim 1, wherein in each container, the section which bends without forming kinks comprises a plurality of corrugations.

5. The stack of containers of claim 1, wherein each container, the at least one tab comprises a first tab and a second tab extending opposite one another from the tip.

* * * * *